(12) United States Patent
Chatelain et al.

(10) Patent No.: US 6,369,065 B1
(45) Date of Patent: Apr. 9, 2002

(54) CD40 SIGNAL BLOCKING AGENT

(75) Inventors: Pierre Chatelain, Brussels; Anne Mignot, Braine-l'Alleud, both of (BE); Mark Taubman, Larchmont, NY (US); Michel Goldman, Brussels (BE)

(73) Assignee: UCB S.A., Brussels (BE)

( * ) Notice: Subject to any disclaimer, the term of this patent is extended or adjusted under 35 U.S.C. 154(b) by 0 days.

(21) Appl. No.: 09/711,620

(22) Filed: Nov. 13, 2000

(30) Foreign Application Priority Data

May 15, 2000 (JP) .......................................... 12-147506

(51) Int. Cl.[7] ............................................ A61K 31/505
(52) U.S. Cl. ...................................................... 514/258
(58) Field of Search ......................................... 514/258

(56) References Cited

U.S. PATENT DOCUMENTS 6,015,578 A    1/2000   Walch

FOREIGN PATENT DOCUMENTS

GB           1148629       4/1969
GB           2 157 684    10/1985

OTHER PUBLICATIONS

Goldman et al., (1999) "Inhibition of the CD40 Pathway of Monocyte Activation by Triazolopyrmidine.", *Clinical Immunology*, vol. 90, No. 3, pp. 232–238.

Taubman, et al., (1999) "Trapidil Inhibits Monocyte Chemoattractant Protein–1 and Macrophage Accumulation after Balloon Arterial Injury in Rabbits" *Laboratory Investigation*, vol. 79, No. 11, pp. 1369–1375.

*Primary Examiner*—Raymond Henley, III
(74) *Attorney, Agent, or Firm*—McDonnell Boehnen Hulbert & Berghoff (57) ABSTRACT

A CD40 signal blocking agent comprising, as an active ingredient, s-triazolo[1,5-a]pyrimidine derivative represented by the following formula (1) or a pharmaceutically acceptable salt thereof, is disclosed (I)

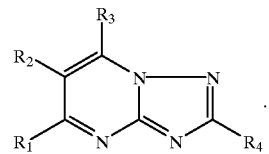

23 Claims, 1 Drawing Sheet

CD40 SIGNAL BLOCKING AGENT

FIELD OF THE INVENTION

The present invention relates to therapeutic agents for life-style related diseases in mammals. More specifically, it relates to CD40 signal blocking agents comprising, as an active ingredient, s-triazolo(1,5-a)pyrimidine derivatives represented by formula (1) or at least one of the pharmaceutically acceptable salts thereof, said blocking agents having at least one of the following effects: a) an effect of blocking the CD40 pathway for monocyte/macrophage activation, b) an effect of suppressing CD40 expression, c) an effect of suppressing IL-6 production, d) an effect of suppressing II-12 production, and e) an effect of suppressing MCP-1 production. It also relates to a method of screening agents that reduce a risk of cardiovascular events.

SUMMARY OF THE RELATED ART

In recent years, with the westernization of life-styles and the aging of the population, cases of heart diseases, cerebrovascular accidents, hypertension, hyperlipemia and ischemic heart diseases are increasing year by year in Japan. In the face of this trend, the Council on Public Health of the Ministry of Health and Welfare (MHW) submitted a report in December 1996 titled "On basic policy in fights against diseases with a focus on life-styles," and emphasized the need of introducing the concept of "life-style related diseases" in measures for preventing diseases and improving physical fitness of Japanese people.

At about the same time, it was reported (Yasue et al., Am. J. Cardiol. 83: 1308–1313, 1999) in a large scale clinical study, Japanese Antiplatelets Myocardial Infarction Study 2 (JAMIS2), by the MHW contract research on cardiovascular diseases 6-shi-1 "A study on the effects of antiplatelet and antithrombotic agents in preventing the recurrence of cardiovascular diseases" study group, that a long-term continuous administration of trapidil (300 mg/day), an s-triazolo[1,5-a]pyrimidine derivative, remarkably reduced the recurrence rate of myocardial infarction in patients with acute myocardial infarction (p=0.0810), and unlike an antiplatelet drug aspirin, it significantly (p=0.0039) reduced the incidence of secondary cardiovascular events. This is attracting attention from the viewpoint of preventing and treating the aggravation of life-style related diseases.

However, though the result on trapidil in JAMIS suggested a mechanism of action different from that of aspirin is involved in the suppression of cardiovascular events secondary to life-style related diseases in particular acute myocardial infarction, the mechanisms has yet to be elucidated.

For trapidil, it is known trapidil and its derivative, an s-triazolo[1,5-a]pyrimidine derivative of formula (1), is an antiplatelet agent, and partially acts as a phosphodiesterase inhibitor and a competitive inhibitor of PDGF receptor. For trapidil in particular, various pharmacological effects have been reported. For example, it suppresses the hyperplasia of the tunica interna in rodent models of tunica interna smear (Ohnishi et al., Life Sci. 31: 2595–2602, 1982; Tiell et al., Artery 12: 33–50, 1983, and the like). AR12463, a trapidil derivative, is known to suppress the progress of aorta lesions in rabbit models of arteriosclerosis (Beitz et al., Biomed. Biochim. Acta. 50: 101–107, 1991). It is also reported that trapidil suppresses restenosis after PTCA (Matsuno et al., Thromb. Haemost. 74: 1591–1596, 1995, and the like) Trapidil is also known to suppress the differentiation of cultured cells including blood smooth muscle (SMC) (Matsuno et al., supra; Benelli et al., JOcul. Pharmacol. Ther. 11: 157–166, 1995; Bonisch et al., Mol. Pharmacol. 54: 241–248, 1998, and the like). The differentiation of many of them are induced by PDGF, and their effects are beginning to be recognized as the inhibition of PDGF receptor. Recently, it was found that trapidil inhibits the protein kinase cascade that is induced by PDGF and activated by cancers (Bonisch et al., supra: Hoshiya and Awazu et al., Hypertension 31: 665–671, 1998). Furthermore, the inhibitory activity of TNF-α sysnthesis was found and the treatment of diseases related to TNF-induced pathological disorders has been reported (Kohyo (National Publication of Translated Version) 11-503434).

The results of JAMIS indicated that mechanisms that cannot be simply explained from the viewpoint of platelet agglutination and/or blood coagulation are involved in the onset of cardiovascular events secondary to acute myocardial infarction. Thus, there is a great need for the elucidation of drug profiles required for drugs suppressing cardiovascular events. The supply of such drug profiles is very important as a profile indispensable for dosage guides as an agent for suppressing cardiovascular events, the choice of the drug to be used in combination, and by extension, as sales promotional activities to medical doctors, or improved drugs to be developed in the future. Furthermore, when the mechanism of action leads to information related to gene expression in the patient, it is also important from the viewpoint of the order made healthcare considered to be a future target.

With regard to suppression of the onset of cardiovascular events, there is a report that demonstrates that the onset of coronary artery diseases can be prevented by cholesterol-lowering therapies, in particular a therapy with HMG-COA reductase inhibitors. It is known, however, that the cholesterol-lowering effect alone is not sufficiently effective for the suppression of events or reducing risks thereof (Progress in Medicine 18(5): 1030–1036, 1998), and thus there is a need for a concept useful for the development of new agents for suppressing cardiovascular events.

DETAILED DESCRIPTION OF THE INVENTION

After intensive research to solve the above problems, the inventors of the present invention have surprisingly found that trapidil blocks CD40 signals, and more specifically that it strongly suppresses the reactivity to CD40 stimulation (ligation) of monocytes, it suppresses the production of IL-6 or IL-12, it suppresses the expression of CD40 in monocytes, and it suppresses the production of MCP-1.

The embodiments of the present invention will now be explained hereinbelow.

Embodiment 1 relates to a CD40 signal blocking agent that is an s-triazolo[1,5-a]pyrimidine derivative represented by formula (1):

or at least one pharmaceutically acceptable salt thereof, wherein $R_1$ is H, halo, $C_1$–$C_4$ alkyl, alkoxyalkyl, aralkyl, aryl, substituted aryl, or $NR_5R_6$;

$R_2$ is H, halo, $C_1$–$C_4$ alkyl, alkenyl, aralkyl, or aryl;

$R_3$ is amino or substituted amino with one substituent or two substituents that are the same or different, which substituents are selected from alkyl, cycloalkyl, alkenyl, hydroxyalkyl, alkylaminoalkyl or alkoxy, an optionally substituted aryl group, an aralkyl group, a heterocyclic group, or $R_3$ is hydrazino, guanidino, tertiary cyclic amino, a linear or branched alkoxy group having 2–4 carbons substituted with a basic group in which said basic group is the above amino group, a substituted amino group, a guanidino group, a hydrazino group or a cyclic amino group, or $NR_7R_8$;

$R_4$ is H, halo, $C_1$–$C_4$ alkyl, alkoxyalkyl, aralkyl, aryl, or substituted aryl;

$R_5$ and $R_6$ are H, $C_1$–$C_5$ linear or branched alkyl groups, or $R_5$ and $R_6$, together with a heteroatom, form a ring;

$R_7$ is $C_4$–$C_9$ linear or branched alky, $C_1$–$C_3$ alkoxy or alkyl substituted aralkyl, 2,5-dioxaheptyl, or 3-oxahexyl;

$R_8$ is H, $C_1$–$C_3$ alkyl, hydroxyethyl, or a hydroxypropyl;

provided that when $R_1$ is $NR_5R_6$ and $R_3$ is $NR_7R_8$, substituents at positions 5 and 7 are interchangeable;

said blocking agent having at least one of the following effects a) to e):
  a) an effect of blocking the CD40 pathway for monocyte/macrophage activation,
  b) an effect of suppressing CD40 expression,
  c) an effect of suppressing IL-6 production,
  d) an effect of suppressing Il-12 production, and
  e) an effect of suppressing MCP-1 production.

The following compound (Ia) or (Ib) is preferred.

Compound (Ia): A compound of formula (1) wherein $R_1$ is H, halo, $C_1$–$C_4$ alkyl, alkoxyalkyl, aralkyl, aryl, substituted aryl; $R_2$ is H, halo, $C_1$–$C_4$ alkyl, alkenyl, aralkyl, or aryl; $R_3$ is amino, substituted amino with the same or different substituents selected from alkyl, cycloalkyl, alkenyl, hydroxyalkyl, alkylaminoalkyl or alkoxy, an optionally substituted aryl group, an aralkyl group, a heterocyclic group, or $R_3$ is hydrazino, guanidino, tertiary cyclic amino, a linear or branched alkoxy group having 2–4 carbons substituted with a basic group in which said basic group is the above amino group, a substituted amino group, a guanidino group, a hydrazino group or a cyclic amino group; and $R_4$ is H, halo, $C_1$–$C_4$ alkyl, alkoxyalkyl, aralkyl, aryl, or substituted aryl.

Compound (Ib): A compound of formula (1) wherein $R_1$ is $NR_5R_6$. $R_5$ and $R_6$ are H, $C_1$–$C_5$ linear or branched alkyl groups, or $R_5$ and $R_6$, together with a heteroatom, form a ring; $R_2$ is H, halo, $C_1$–$C_4$ alkyl, and $R_3$ is $NR_7R_8$. $R_7$ is $C_4$–$C_9$ linear or branched alkyl, $C_1$–$C_3$ alkoxy or alkyl substituted aralkyl, 2,5-dioxaheptyl, or 3-oxahexyl, $R_8$ is H, $C_1$–$C_3$ alkyl, hydroxyethyl, or a hydroxypropyl; and $R_4$ is H, halo, or $C_1$–$C_4$ alkyl. The substituents at positions 5 and 7 are interchangeable.

More preferably, compound (Ia'): A compound of formula (1) wherein $R_1$ is H, methyl, ethyl, or phenyl; $R_2$ is H, chloro, or bromo; $R_3$ is diethylamino, isobutylamino, benzylamino, furfurylamino, n-amylamino, diethanolamino, piperidino, o-chloroanilino, p-carboethoxyanilino, or β-diethylamino-ethoxy; and $R_4$ is H, methyl, ethyl, isopropyl, phenyl, or 3,4,5-trimethoxyphenyl;

Compound (Ib'): A compound of formula (1) wherein $R_1$ is piperidino, diethylamino, or morpholino; $R_2$ is H; $R_3$ is N-(n-butyl)-N-(β-hydroxyethyl)-amino, N-(n-pentyl)-N-(β-hydroxyethyl)-amino, N-(n-hexyl)-N-(β-hydroxyethyl)-amino, or a N-(ethoxyethyl)-N-(β-hydroxyethyl)-amino; and $R_4$ is H.

As most preferred compounds, there can be mentioned 7-diethylamino-s-triazolo[1,5-a]pyrimidine, 7-benzylamino-s-triazolo[1,5-a]pyrimidine, 2-ethyl-5-methyl-7-diethylamino-s-triazolo[1,5-a]pyrimidine, 5-methyl-6-chloro-7-furfurylamino-s-triazolo[1,5-a]pyrimidine, 5-methyl-6-bromo-7-diethylamino-s-triazolo[1,5-a]pyrimidine, 5-methyl-7-(β-diethylamino-ethoxy)-s-triazolo[1,5-a]pyrimidine, 2-isopropyl-5-methyl-7-piperidino-s-triazolo[1,5-a]pyrimidine, 5-methyl-7-n-amyl-amino-s-triazolo[1,5-a]pyrimidine, 2-(3',4',5'-trimethoxy-phenyl)-5-methyl-7-piperidino-s-triazolo[1,5-a]pyrimidine, 5-phenyl-7-diethanolamino-s-triazolo[1,5-a]pyrimidine, 2-phenyl-5-methyl-7-piperidino-s-triazolo[1,5-a]pyrimidine, 5-methyl-7-(o-chloro-anilino)-s-triazolo[1,5-a]pyrimidine, 7-(p-carboethoxy-anilino)-5-methyl-s-triazolo[1,5-a]pyrimidine, N,N-diethyl-N'-[5-methyl-6-bromo-s-triazolo[1,5-a]pyrimidinyl-(7)]-propylene diamine, 5-methyl-7-benzylamino-s-triazolo[1,5-a]pyrimidine, 2,5-dimethyl-7-furfuryl-amino-s-triazolo[1,5-a]pyrimidine, 2,5-dimethyl-7-benzylamino-s-triazolo[1,5-a]pyrimidine, 2,5-dimethyl-7-piperidino-s-triazolo[1,5-a]pyrimidine, 5-methyl-7-diethylamino-s-triazolo[1,5-a]pyrimidine, 2,5-dimethyl-7-isobutyl-amino-s-triazolo[1,5-a]pyrimidine, 5-piperidino-7-(N-(n-pentyl)-N-(β-hydroxyethyl)-amino)-s-triazolo[1,5-a]pyrimidine, 5-diethylamino-7-(N-(n-pentyl)-N-(β-hydroxyethyl)-amino)-s-triazolo[1,5-a]pyrimidine, 5-diethylamino-7-(N-(n-hexyl)-N-(β-hydroxyethyl)-amino)-s-triazolo[1,5-a]pyrimidine, 5-piperidino-7-(N-(n-hexyl)-N-(β-hydroxyethyl)-amino)-s-triazolo[1,5-a]pyrimidine, 5-morpholino-7-(N-(n-butyl)-N-(β-hydroxyethyl)-amino)-s-triazolo[1,5-a]pyrimidine, 5-piperidino-7-(N-(ethoxyethyl)-N-(β-hydroxyethyl)-amino)-s-triazolo[1,5-a]pyrimidine, and 5-diethylamino-7-(ethoxyethyl)-N-(β-hydroxyethyl)-amino)-s-triazolo[1,5-a]pyrimidine.

As pharmaceutically acceptable salts of the compounds of formula (1), there can be mentioned salts with hydrochloric acid, hydrobromic acid, hydriodic acid, sulfuric acid, nitric acid, oxalic acid, malonic acid, tartaric acid and the like.

Furthermore, the hydrates or solvates (ethyl alcohol, acetic acid etc.) of the compounds of formula (1) or salts thereof are also included in the present invention.

To each compound of the above preferred embodiments, the following embodiments are further imparted individually: each compound has two or more of the effects a) to e), more preferably at least effects a) and e), more preferably three or more, more preferably four or more, and most preferably all the five effects.

Embodiment 2 is a preventive and/or therapeutic agent for cardiovascular events in life-style related diseases, said agent comprising the drug of Embodiment 1 as an active ingredient.

More preferably, it is a preventive and/or therapeutic agent for cardiovascular events in life-style related diseases in which the "life-style related disease" is insulin non-dependent diabetes mellitus, obesity, hyperlipemia, cardiovascular diseases (except congenital diseases), and alcoholic liver diseases. More preferably, it is an agent for suppressing cardiovascular events based on hyperlipemia, specifically hipercholesterolemia, or it is an agent for suppressing cardiovascular events based on cardiovascular diseases, specifically coronary artery diseases (CAD: one selected from coronary atherosclerosis, acute or chronic myocardial infarction, angina pectoris, and/or heart failure), or cerebrovascular diseases (for example, one selected from intracranial and/or extracranial atherosclerosis, attack and transient ischemic attack).

With regard to each of the above "cardiovascular events," the diseases are selected from pathological states such as cardiovascular death (lethal myocardial infarction or sudden cardiac death etc.), non-lethal myocardial infarction, reinfarction, unstable angina, transient ischemic attack, congestive heart failure, stroke, cerebral infarction, and syncope, or treatments such as Coronary artery bypass graft (CABG), percutaneous transluminal coronary angioplasty (PTCA), and stents, and more preferably diseases selected from cardiovascular death (lethal myocardial infarction or sudden cardiac death), non-lethal myocardial infarction, reinfarction, unstable angina, and transient ischemic attack are preferred.

For suppression of cardiovascular events, the event suppressive agents that reduce the onset of cardiovascular events within one year after the start of the treatment are preferred, and the event suppressive agents that reduce the onset of cardiovascular events within six months after the start of the treatment are more preferred.

Preferred are said preventive and/or therapeutic agents that are for long-term continuous administration.

Incidentally, these preferred descriptions can be defined as an embodiment of a new lower conception by combining them individually.

Embodiment 3 is a CD40 signal blocking agent for life-style related diseases in mammals, said agent comprising the compound of formula (1) as an active ingredient. The definitions of life-style related diseases are the same as in Embodiment 2. More preferred is said CD40 signal blocking agent wherein the compound of formula (1) is trapidil or AR12463. More preferred is said CD40 signal blocking agent that is used for long-term continuous administration.

Embodiment 4 is a method of screening agents that reduce a risk of cardiovascular events in life-style related diseases, wherein a compound or a agent having at least an effect of blocking CD signals is compared with a trapidil. Preferably, it is a method that comprises screening agents that are equal to or better than trapidil in a comparison measurement.

More preferably, it is a screening method comprising at least one or more of the following comparison measurements. More preferably, there can be mentioned a screening method comprising, at least, either of the following 1) and 2), and 5), and more preferably a screening method further combining either of 3) and 4). Although a direct comparison of the test drug with trapidil is preferred in the comparison measurement, a direct comparison can also be made using the following specific suppression strength established based on the experimental example of the present invention, and such methods are also included in the present invention.

1) the comparison measurement of CD40 down regulation,
2) the comparison measurement of suppression of CD40 mRNA expression,
3) the comparison measurement of suppression of IL-6 production by monocytes,
4) the comparison measurement of suppression of II-12 production by monocytes, and
5) the comparison measurement of suppression of MCP-1 production.

Each of them will be explained in more detail hereinbelow.

1) The Comparison Measurement of CD40 Down Regulation

CD40 expression by monocytes is evaluated using the dose dependent suppression by the drug as an index both at the baseline level and/or during upregulation.

Specifically, (1) at the baseline level, the test drug has a suppression effect of 30% or higher at either concentration of 100 $\mu$M–10 $\mu$M, preferably 90% or higher at 100 $\mu$M, or 30% or higher at 10 $\mu$M, and/or (2) during up regulation, the test drug has a suppression effect of 30% or higher at either concentration of 100 $\mu$M–20 $\mu$M, preferably 80% or higher at 100 $\mu$M, or 60% or higher at 60 $\mu$M, is used as an index. These suppression effects can be measured, for example, by flow cytometry described in the experimental example below.

2) The Comparison Measurement of Suppression of CD40 mRNA Expression

In human monocytes, for example, the dose dependent suppression by the drug of CD40 mRNA expression is used as an index. Specifically, a significant suppression is used as an index when CD40 mRNA expression is observed by RT-PCR with the test drug at 100 $\mu$M or lower for at least either of at the baseline level and during upregulation.

3) The Comparison Measurement of Suppression of IL-6 Production By Monocytes

The dose dependent suppression effect by the test drug of IL-6 production into the culture of monocytes by co-cultivation with cells (for example, 3T6 fibroblasts) stimulated with CD40L, for example cells transformed with the CD40L gene, are comparison measured.

Specifically, it is a method of determination that uses as an index that the test drug has a suppression effect of 50% or higher at either concentration of 100 $\mu$M–10 $\mu$M, preferably 90% or higher at 80–100 $\mu$M, or 50% or higher at 10–20 $\mu$M. More preferably, it is a method of determination that has further added, as an index, a characteristic that it does not affect IL-6 production by LPS stimulation.

4) The Comparison Measurement of Suppression of IL-12 Production By Monocytes

The dose dependent suppression effect by the test drug of IL-12 production into the culture of monocytes by co-cultivation with cells stimulated with CD40L, for example cells transformed with the CD40L gene, are comparison measured.

Specifically, it is a method of determination that uses as an index that the test drug has a suppression effect of 50% or higher at either concentration of 100 $\mu$M–10 $\mu$M, preferably 80% or higher at 80–100 $\mu$M, or 50% or higher at 10–20 $\mu$M. More preferably, it is a method of determination that has further added, as an index, a characteristic that it does not affect IL-12 production by LPS stimulation.

5) The Comparison Measurement of Suppression of MCP-1 Production

In an artery damaged model of the high-fat diet animals, the degree of suppression by the test drug of MCP-1 production at the damaged site is comparison determined. In said damaged model as a specific embodiment, the test drug is administered for a predetermined period of time from before to after the artery smear, and the degree of suppression of MCP-1 expression and, as needed, macrophage migration and infiltration at the damaged site of the artery is observed.

Preferably, the artery smear model is a femoral artery balloon smear model of the high-fat diet rabbits, and the test drug is administered subcutaneously on the day before and the day of treatment and for 6 days after the treatment, and on day 7 the degree of suppression is observed.

Specifically, when the test drug is subcutaneously injected at a dose of 60 mg/kg/day or lower, the degree of suppression of 50% or higher, in particular 75% or higher in MCP-1 expression and/or macrophage migration at the artery damaged site on day 7 is used as an index.

Embodiment 5 is a suppression agent of MCP-1 production and/or a suppression agent of macrophage infiltration at the damaged site of the blood vessel, said agent comprising the compound of formula (1) or a pharmaceutically acceptable salt thereof as an active ingredient. More preferably, it is a suppression agent of MCP-1 production and/or a suppression agent of macrophage infiltration in mammals at the hyperlipemia state.

It is also a suppression agent of MCP-1 production and/or a suppression agent of macrophage infiltration for the suppression of atherogenic plaque formation at the damaged site of the blood vessel.

Embodiment 6 is a CD40 signal blocking agent for the suppression of atherogenic plaque formation at the damaged site of the blood vessel, said agent comprising the compound of formula (1) or a pharmaceutically acceptable salt thereof as an active ingredient.

Embodiment 7 is a CD40 blocking agent as a reagent comprising the compound of formula (1) or a pharmaceutically acceptable salt thereof as an active ingredient. The reagent as used herein means a reagent used to utilize the blocking effect of CD40 signal in general, and there can be mentioned, for example, reagents used to judge the involvement of CD40 signals in various biochemical reactions and pathological states in mammals. It will also be possible to screen compounds that promote or control CD40 signal transduction by utilizing the CD40 signal blocking environment mimetically created by adding it to various in vitro or in vivo systems.

For the compounds of formula (1) in the above Embodiments 2, 3, 5, 6, and 7, the definition of the preferred compound in Embodiment 1 can be applied as the preferred compound.

In accordance with the present invention, the compound of formula (1) is a trapidil derivative, and its synthesis, pharmacological actions, and toxicity studies have been disclosed in GB1148629 or Japanese Unexamined Patent Publication (Kokai) No. 60-224692.

The suppression effects a) to e) can be confirmed by, for example, the determination methods 1) to 5) in the above screening method.

"Mammals" as used herein includes primates including humans, and pet animals such as dogs and cats, and preferably they are humans.

"Life-style related diseases" as used herein means "a group of diseases in which life-style such as eating habits, habits of exercises, rests, smoking, and drinking is involved in the onset and/or progression of the diseases," and specifically there can be mentioned insulin non-dependent diabetes mellitus, obesity, hyperlipemia, hyper uric acidemia, cardiovascular diseases (except congenital diseases), alcoholic liver diseases and the like.

Preferably, they are pathological states having one or more than one risk factor such as hypercholesterolemia, coronary artery diseases (CAD), family of coronary artery diseases, hypertension, diabetes mellitus, smoking habits, cerebrovascular diseases and/or being a male.

Among them, "coronary artery diseases (CAD)" means diseases such as coronary atherosclerosis, acute or chronic myocardial infarction, angina pectoris, and/or heart failure. "Cerebrovascular diseases" means diseases such as intracranial and/or extracranial atherosclerosis, attack and transient ischemic attack.

"Cardiovascular events" means pathological states such as cardiovascular death (lethal myocardial infarction or sudden cardiac death etc.), non-lethal myocardial infarction, reinfarction, unstable angina, and transient ischemic attack, congestive heart failure, stroke, cerebral infarction, and syncope, or treatments such as coronary artery bypass graft (CABG), percutaneous transluminal coronary angioplasty (PTCA), and stents. Preferably they are diseases selected from cardiovascular death (lethal myocardial infarction or sudden cardiac death), non-lethal myocardial infarction, reinfarction, unstable angina, and transient ischemic attack.

More preferably, the event suppressive agents that reduce the onset of cardiovascular events within one year after the start of the treatment are preferred, and the event suppressive agents that reduce the onset of cardiovascular events within six months after the start of the treatment are more preferred.

The embodiments related to the above "life-style related diseases" and "cardiovascular events" may be combined to be defined as new embodiments. "Long-term continuous administration" means a dosage regimen in which a drug is continuously administered for a period of three months or longer, preferably six months or longer, more preferably one year or longer, and more preferably two years or longer.

"Damaged site of the blood vessel" means a damaged site of the artery or the vein, and preferably the damaged site of the arterial vessel. As the specific damaged site, there can be mentioned a defective site at the endothelial cell in the artery, or thrombus attachment site in the artery.

The present invention will now be explained with reference to the specific examples of trapidil of the present invention. It should be noted, however, that the present invention is not limited by these examples in any way.

EXAMPLE 1

Tablets

| i)   | Japanese Pharmacopeia trapidil | 50 g              |
|------|-------------------------------|-------------------|
| ii)  | Lactose                       | a suitable amount |
| iii) | Crystalline cellulose         | 60 g              |
| iv)  | Potato starch                 | 54 g              |
| v)   | Magnesium stearate            | 2 g               |

Among the above, i) to iv) are mixed, to which is added a previously taken aliquot of iv) as a 10% glue to produce granules, which are dried. Then, v) is added thereto, mixed, and formulated into a CD40 signal blocking agent containing 200 mg (50 mg as trapidil) per tablet. Sugar coating according to a standard method can also be made.

EXAMPLE 2

Capsules

| i)   | Japanese Pharmacopeia trapidil | 50 g              |
|------|-------------------------------|-------------------|
| ii)  | Calcium phosphate, dibasic    | 50 g              |
| iii) | Aluminium silicate            | a suitable amount |
| iv)  | Crystalline cellulose         | 60 g              |
| v)   | Magnesium stearate            | 2 g               |

The above i) to v) are mixed, and further sieved and mixed well. Then a CD40 signal blocking agent containing 200 mg per capsule is formulated according to a standard method.

EXAMPLE 3

Injections 100 g of crystalline Japanese Pharmacopeia trapidil is weighed out, and is dissolved in 2 L of water for injection, which is then formulated into a CD40 signal blocking agent containing 100 mg/2 ml per ampoule according to a standard method.

EXAMPLE 4

Sustained Release Tablets

Japanese Pharmacopeia trapidil (1200 g), microcrystalline cellulose (540 g), and lactose (230 g) are mixed and kneaded with a solution in which hydroxypropyl cellulose (30 g) was dissolved in ethanol (270 g). After extruding through a 0.8 mm$\phi$ screen, it is formulated into spherical granules. After drying at 55° C., they are sized with a 14–30 mesh to formulate raw granules.

The raw granules are subjected to film coating to 10% of the weight of the raw granules using a coating solution of the following composition (1) according to a standard method to apply a coating of the first layer. Furthermore, using a coating solution of the following composition (2) according to a standard method, a coating of the second layer is applied to 20% of the weight of the raw granules to formulate coated granules. To 325 g of these coated granules, microcrystalline cellulose (136 g) is mixed, to which are added magnesium stearate (2.5 g) and talc (2.5 g), and then mixed.

According to a standard method, a CD40 signal blocking agent containing 466 mg (150 mg as trapidil) per tablet is obtained.

| Composition (1) | |
|---|---|
| Hydroxypropyl methyl cellulose | 5% |
| Purified water | 95% |
| Total | 100% |
| Composition (2) | |
| Ethyl cellulose | 6.0% |
| Glycerin fatty acid ester | 1.5% |
| Talc | 0.5% |
| Ethanol | 90.0% |
| Purified water | 2.0% |
| Total | 100.0% |

EXAMPLE 5

Sustained Release Tablets

| i) | Japanese Pharmacopeia trapidil | 300 mg |
|---|---|---|
| ii) | Methocel K100 MCR | 200 mg |
| iii) | Anhydrous Na$_2$CO$_3$ | 75 mg |
| iv) | Avicel pH102 | 16 mg |
| v) | Aerodil 200 | 3 mg |
| vi) | Magnesium stearate | 6 mg |

The above ingredients are mixed according to a standard method, and then are compressed into 200 mg tablets to formulate sustained release tablets of the present invention.

EXAMPLE 6

Commercially available Rocornal tablets (50 mg of sugar-coated tablets), Rocornal tablets 100 mg (film-coated tablets), and Rocornal parvules (I g contains 100 mg of Japanese Pharmacopeia trapidil) are used as formulations to carry out the present invention.

EXPERIMENTS

The present invention will now be explained with trapidil as a representative example, but, it should be noted, that other drugs having a CD40 signal blocking effect, in particular the triazole pyrimidine derivative of formula (1), can be used in the experiment. In the following experiment, the culture system used an RPMI 1640 medium supplemented with 10% FBS, 20 $\mu$M gentamycin, 50 $\mu$M 2-ME, 1% non-essential amino acids. Recombinant interferon γ (IFNγ) used was from Genzyme Corp. and LPS (O127; B4) was from Sigma Chemical Co., Ltd. Trapidil powders were dissolved in DMSO and diluted in RPMI. As a control, 0.1% DMSO solution was used.

Preparation of Monocytes

From a plurality of normal healthy humans, peripheral blood mononuclear cells (PBMC) were recovered according to the method of Pradier et al., Eur. J. Immunol. 26: 3048–3054, 1996. Monocytes were purified by incubating PBMC at 4° C. for 1 hour, and then by centrifuging at 100 g for a short period of time. The precipitate was suspended in a culture medium and plated. The purity of the monocytes obtained was evaluated by staining with a May-Grunwald-Giemsa stain under a microscope (the purity was about 80%).

Stimulation of Monocytes

The monocytes obtained ($5\times10^5$/ml) were stimulated with LPS (10 ng/ml) or IFNγ(1 ng/ml) for 24 hours. CD40 stimulation (Ligation) was carried out by co-culturing with $5\times10^4$ /ml of fibroblasts (3T6-CD40L) into which CD40 ligand cDNA had been transduced or with parent fibroblasts (3T6) for 72 hours. Culturing was carried out in the presence of DMSO or a triazolopyrimidine derivative in DMSO (10–100 $\mu$M).

Cytokeine Assay

The culture supernatant of monocytes stimulated with LPS or CD40 ligand was collected, and the insoluble mater was removed by centrifuging, followed by freezing at −70° C. Soluble IL-6, IL-12 and TNFα were determined using specific ELISA kit (BioSpurce, Europe, SA).

Flow Cytometry Analysis

Monocytes were stained with a FITC-labeled antibody (Biosource), and the amount of CD40 expressed was determined by the FACScan cytometer (Becton-Dickinson).

Analysis of CD40 mRNA Expression By PCR

Monocyetes ($5\times10^5$/ml) were stimulated or not stimulated with 1 ng/ml IFNγ in the presence of 100 $\mu$M of trapidil or 0.1% DMSO. Culturing was stopped at 4 hours. Cellular RNA was extracted with the TriPure Isolation reagent (Boehringer Mannheim). After reverse transcription, 28 cycles of PCR (94° C. for 20 seconds, 55° C. for 20 seconds, and 72° C. for 30 seconds) of CD40 cDNA and β actin were carried out. The primer of CD40 (Gibco, manufactured by Life Technologies) was 5' GTCCATCCAGAACCACCCAC 3', and the antisense primer used was 3' GGTCAGCCGAA-GAAGAGGTT 5'.

RESULT OF THE EXPERIMENT (1) Downregulation of CD40 expression

Figure 2:
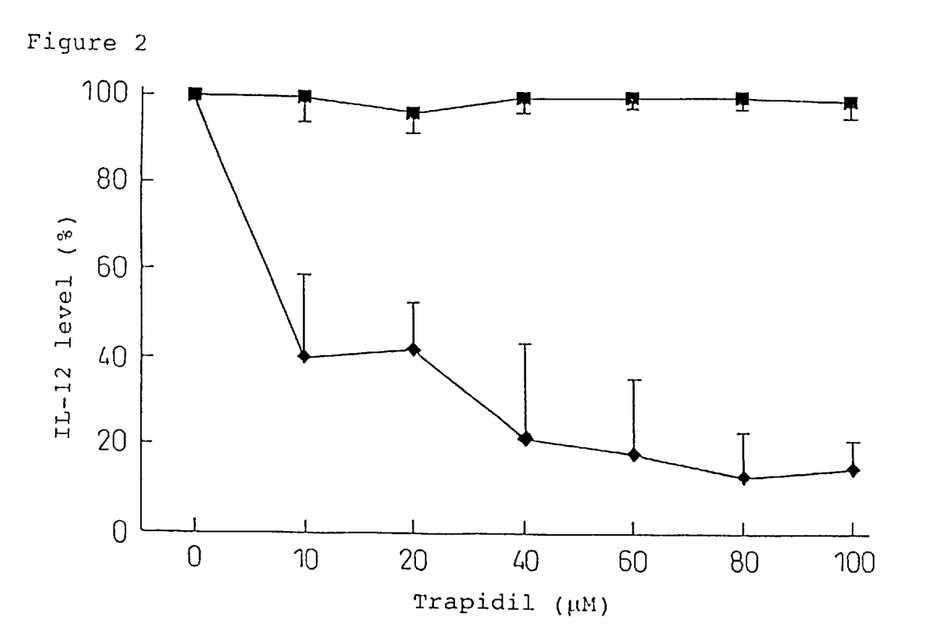
FIG. 2 is a graph showing a dose dependent suppression of IL-12 production by trapidil.

The effects of the drug on CD40 expression on the membrane surface of monocytes at the baseline level and under stimulation with recombinant IFNγ (rIFNγ) were analyzed. It is known that rIFNγ upregulates CD40 expression in monocytes (Klener et al., J. Immunol. 155: 4917–4925, 1995). The result is shown in FIG. 2 and Table 1. Monocytes were not stimulated or stimulated with rIFNγ (1 ng/ml) in the presence of a predetermined concentration of trapidil for 24 hours, and were stained for a FITC-labeled CD40 antibody. The experimental values indicate the average percentage of mean fluorescence intensity (MFI) (the value in the absence of trapidil is set at 100%) of triplicate determinations.

TABLE 1

| Trapidil (µM) | CD 40% | |
| --- | --- | --- |
| | Baseline level | Under IFNγ stimulation |
| 10 | 71.99 | 86.71 |
| 20 | 46.53 | 71.07 |
| 60 | 23.14 | 32.73 |
| 100 | 8.7 | 17.91 |

Trapidil suppressed CD40 expression in monocytes at concentrations of 10–100 µM in a dose dependent manner both at the baseline level and under rIFNγ stimulation. It has been confirmed that even in the presence of the highest concentration of trapidil about 90% of the viability of cells is retained as determined by the 7-AAD staining, and thus the present suppression effect is not related to nonspecific cytotoxicity.

(2) Suppression of CD40 mRNA Expression

Monocytes were cultured under no stimulation or stimulation with rIFNγ (1 ng/ml) in the presence of trapidil (100 µM) or a 0.1% DMSO solution for 4 hours. cDNA prepared under both conditions was subjected to amplification of CD40 or β actin by RT-PCR.

Trapidil significantly suppressed the accumulation of CD40 mRNA under both conditions of the baseline level and rIFNγ stimulation. Thus, it was shown that trapidil suppresses the expression of the CD40 gene in human monocytes.

(3) Suppression of IL-6 Production

In the absence of trapidil, IL-6 production by monocytes in the culture alone or under co-cultivation with untreated fibroblasts (3T6) was 0.01 ng/ml. Under stimulation with LPS (10 ng/ml), it was 3.37 ng/ml, and under 3T6-CD40L stimulation it was 1.5 ng/ml.

Figure 1:
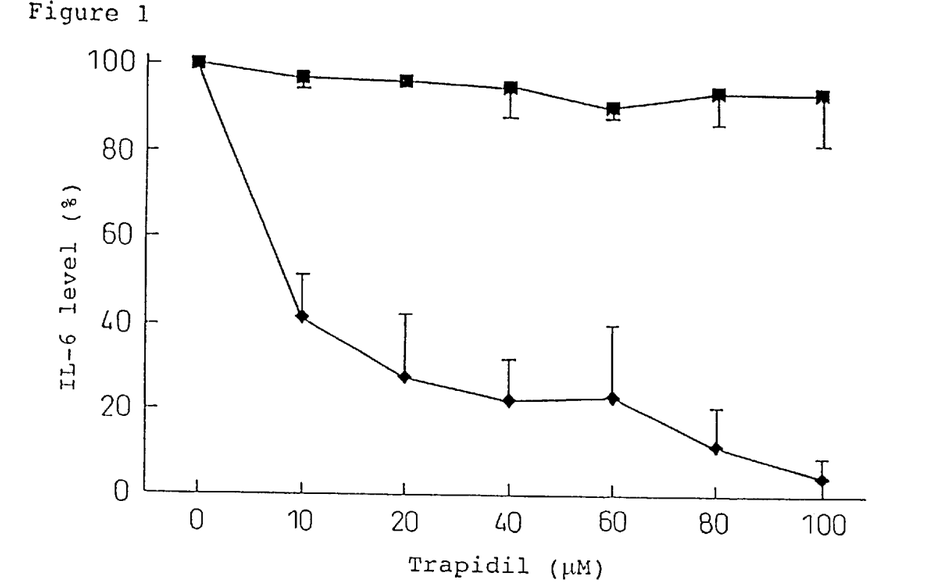
FIG. 1 is a graph showing a dose dependent suppression of IL-6 production by trapidil.

As shown in FIG. 1, trapidil suppressed, in a dose dependent manner in the concentration range of 10–100 µM, IL-6 production (♦ in the figure) by monocytes ($5 \times 10^5$/ml) stimulated by co-cultivating with 3T6-CD40L ($5 \times 10^4$/ml). However, it did not affect IL-6 production (black squares in the figure) by LPS stimulation.

(4) Suppression of IL-12 Production

In the absence of triazolopyrimidine, IL-12 production by monocytes under no stimulation was 0.003 ng/ml or lower. Under stimulation with LPS (10 ng/ml), it was 1.4 ng/ml, and under 3T6-CD40L stimulation it was 1.3 ng/ml.

Trapidil suppressed, in a dose dependent manner in the concentration range of 10–100 µM, IL-12 production (♦ in the figure) by monocytes ($5 \times 10^5$ /ml) stimulated by co-cultivating with 3T6-CD40L ($5 \times 10^4$/ml) (FIG. 2). However, it did not affect IL-12 production (black squares in the figure) by LPS stimulation.

In both of (3) and (4), a maximum suppression of 90% or higher was shown in the dosage range of 80–100 µM trapidil, and a suppression ratio of about 50% was shown in the dosage range of 10–20 µM which is equal to clinical doses.

The above indicated that trapidil strongly inhibits the activation of monocytes through the CD40 pathway.

Since trapidil suppressed TNFα production by monocytes and this suppression was exhibited to TNFα production by not only IFNγ stimulation but LPS stimulation, the suppression of TNFα production seems to have a mechanism different from that of IL-6 and IL-12.

(5) Suppression of Macrophage Accumulation and MCP-1 Production

New Zealand white rabbits (4.0±0.2 kg) were fed a normal rabbit diet supplemented with 2% cholesterol and 6% peanut oil from one month before the treatment of aorta balloon smear. The rabbits were divided into the control group (n=15) and the trapidil treatment group (n=12). Trapidil (30 mg/kg, 60 mg/kg/day) was subcutaneous injected every 12 hours on the day before and the day of treatment and for 6 days after treatment.

The first administration on the day of treatment was carried out one hour before the treatment. To all rabbits, 200 U/kg of heparin sodium was rapidly administered intravenously before the balloon smear treatment. Balloon smear was performed at the bilateral femoral arteries by inserting a 2.5 mm ballooned catheter (manufactured by Advanced Cardiovascular Systems, Inc., Temecula, Calif.) from the right carotid artery according to the method of Gertz et al., Exp. Mol. Pathol. 59: 225–243, 1993, and Sarembock et al., Circulation 80: 1029–1040, 1989.

Six days after the treatment, the rabbits were anesthetized with pentobarbital sodium, and the bilateral femoral arteries were perfused with PBS, pH 7.4, containing 4% paraformaldehyde at a pressure of 100 mmHg at room temperature for 15 minutes. After 2–3 cm sections were excised from the femoral arteries, they were fixed in PBS, pH 7.4, containing 4% paraformaldehyde, dissected at an interval of 2 mm, dehydrated with ethanol and xylene, and embedded in paraffin. 29 blood vessels from the control and 21 blood vessels from the trapidil administration group were subjected to analysis.

For the determination of cholesterol, 3 ml of serum was collected from the auricular veins before the animals were sacrificed. Cholesterol levels were determined using the BM/Hitachi 747 analyzer by the Boehringer Chloresterol Method.

As in a report by Gertz et al., significant macrophage infiltration was observed: about 10% in the tunica interna of the damaged arteries and 8% in the media. Trapidil suppressed macrophage infiltration in the media and the tunica interna of the arteries by 75%. Similarly, it suppressed MCP-1 production in the media and the tunica interna by 75% (Table 2).

TABLE 2

| | No. of blood vessels | Mean | SEM | p value |
| --- | --- | --- | --- | --- |
| Macrophage | | | | |
| Control | 29 | 0.100 | 0.028 | |
| Trapidil | 21 | 0.025 | 0.002 | 0.0038 |
| MCP-1 | | | | |
| Control | 29 | 0.101 | 0.028 | |
| Trapidil | 21 | 0.026 | 0.002 | 0.016 |

Although very little was known for mediators between major cell types in atherogenic plaques, a very important regulation rule was established recently for CD40 signals in the onset of arteriosclerosis by Francois et al. (Nature, 394, Jul. 9, 1998). The article describes that CD40 signals not only expand the damaged site but regulate the function of blood vessel cells involved in the acute progression of arteriosclerosis including emboli that suddenly cause unstable angina, acute myocardial infarction or the like, and the function of macrophages related to the acute onset of arteriosclerosis.

Furthermore, the CD40/CD40L pathway is involved in various inflammatory diseases in which immunological abnormality plays a part such as multiple myeloma, rheumatoid arthritis, and graft rejection. Hence, efforts have been made to develop biological or scientific means to block this pathway. However, the major result is anti-CD40L (CD154) antibody, of which effectiveness has been observed in experimental autoimmunological models of encephalomyelitis, collagen-induced arthritis, graft rejection, and atherosclerosis.

In another attempt, blocking agents for CD40L, activated T cells, are under study, but blocking agents of the CD40/CD40L pathway are not attracting much attention, and there are no reports on the pharmaceutical products that have an effect on low molecular weight compounds and that were safely prescribed, or on specific clinical effects, in particular the effects on cardiovascular events in life-style related diseases. The present invention is a specific pharmaceutical product for which the relation to the above was found for the first time under these circumstances, and drug profiles deduced from the present invention have important feasibility in development of pharmaceutical products.

Furthermore, interestingly in the present experiment, trapidil exhibited a significant effect of suppressing macrophage infiltration and MCP-1 production. The effect was exhibited at concentrations that do not affect lipids in the blood, in particular serum cholesterol that is considered, in recent years, to be the greatest risk factor of ischemic heart diseases. Therefore, the above improvement effect of the present invention is believed to be independent of improvement in serum lipids. Thus, unlike therapies of lowering cholesterol by the conventional HMG-CoA reductase inhibitor etc., the agent of the present invention that suppresses MCP-1 production is believed to be also useful as a preventive and/or therapeutic agent for cardiovascular events that ameliorate further risk factors.

The CD40 signal blocking agent or the suppressive agent of cardiovascular events of the present invention can be administered alone or in combination with other drugs used for suppressing cardiovascular events.

In the case of drugs containing trapidil as an active ingredient, for example, the unit dosage as trapidil is 10–500 mg, and the total daily dosage is 30–3000 mg for oral administration, preferably 50–600 mg, and more preferably 100–500 mg. In the case of intravenous administration, 1 mg to 10 mg per kg body weight is appropriate. These can be administered in one to a plurality of subdivided doses, and they may be increased or decreased depending on the disease conditions etc.

Most preferred unit dosage is 10 mg, 50 mg, 100 mg, 200 mg, 300 mg, 400 mg, or 500 mg, but in the case of sustained release formulations, 700 mg, 800 mg, 900 mg, 1000 mg, 1100 mg, or 1200 mg can also be used. Normally, 100 mg/dose/adult is orally administered three times per day. Preferred dosage forms are tablets, sugar coated tablets, sustained release tablets, film coated tablets, parvules, granules, powders, capsules, syrups, elixirs, poti, and the like as orally administered formulations. As parenterally administered formulations, injections (liquids for injection, solids for injection to be prepared before use) for intravenous/intraarterial/intradermal/subcutaneous administration, intradermal implants may be mentioned, and as transmucously administered formulations, sublingual tablets, chewing gum, suppositories and the like may be mentioned.

Suitable additives used for solid or liquid dosage forms include excipients such as gelatin, starch, cellulose or its derivatives, lactose, sucrose, sorbitol, mannitol etc., binders such as carboxymethyl cellulose, potato starch, polyvinyl pyrrolidones, polyethylene glycols, gum arabic etc., lubricants such as magnesium stearate, talc, silica etc., water-insoluble inorganic substances such as dibasic calcium phosphate, calcium phosphate etc., glucose, others, disintegrants, emulsifiers, dispersants, suspensions, stabilizers, preservatives, colorants, buffers, or suitable solvents (sterile distilled water etc.) and the like may be mentiond, and they can be combined, as appropriate, to make solid or liquid formulations. In the case of solid oral formulations, various additives may be used to control suitable particle size distributions of active ingredients that provide a specific release rate or a specific release state.

As examples of sustained release formulations or prolonged action formulations, there can be used the formulation/dosage regimens and specific formulations disclosed in Japanese Unexamined Patent Publication (Kokai) No. 64-63521 (in particular, claims 1–7 and Examples 1–3), Japanese Unexamined Patent Publication (Kokai) No. 5-139975 (in particular, claims 1 and Examples 1 to 9), Japanese Unexamined Patent Publication (Kokai) No. 7-2649 (in particular, claims 1–16 and Example 2), Japanese Unexamined Patent Publication (Kokai) No. 7-53379 (in particular, claims 1–2 and Examples 1 to 9), WO 96/32111 (in particular, sustained release tablets in the formulation example), the implant technology in WO 98/36784, and WO 98/41194 (in particular, formulation J in claims 1–10 and Table 11 of Example 5, formulation W, X, and Y in Table 26 in Example 12).

The combined use may be carried out simultaneously with the suppressing agent of the present invention or with an interval in between, and it can be carried out according to a predetermined protocol adapted to the patient's condition for a certain period of time or the entire period of the long-term continuous administration. As the drugs to be used in combination, there can be mentioned one or more drugs selected from the group consisting of lipid lowering drugs such as HMG-CoA reductase inhibitors (pravastatin, simvastatin, lovastatin, fluvastatin, fluindostatin, cerivastatin, itavastatin, atorvastatin etc. and among them, pravastatin, lovastatin, simvastatin, and atorvastatin are preferred), anion exchange resins (cholestyramine, cholestyramide, etc.), fibrate drugs (chlofibrate, clinofibrate), and nicotinic acid drugs. HMG-CoA reductase inhibitors are preferred.

The amount of HMG-CoA reductase inhibitors used in combination is about 1–2000 mg for pravastatin, lovastatin, simvastatin, atorvastatin, etc., preferably the administration of 4–200 mg gives a satisfactory result. It is advantageous for the combined use to start at a lower dosage and then gradually increase to higher dosages.

Other drugs that can be used in combination include β blockers (proctolol, metoprolol, timolol, sotatol, propranolol, oxprenol, etc.), Ca blockers (nifedipine, verapamil, diltiazem, etc.), nitro formulations, and angiotensin converting enzyme inhibitors (captopril, licinopril, etc.).

The suppressing agent of cardiovascular events of the present invention can contain generally known pharmaceutically acceptable salts, for example alkali metal salts, or other common basic salts, or acid addition salts.

The pharmaceutical drugs of the present invention can be administered for a long time, i.e., as long as there remains a risk of onset of cardiovascular events or the conditions persist. As such formulations, sustained release forms in which a predetermined amount can be administered every week, every two weeks, or every month can also be used.

The suppressive agent of cardiovascular events of the present invention can be administered for a long time to patients using as a guidance the large scale clinical trial or cardiovascular events reported in Am. J. Cardiol. 38: 1308–1313, 1999. By such a long-term administration, the treatment of patients as well as its significant therapeutic effects can be confirmed.

The CD40 signal blocking agents of the present invention suppress the onset of cardiovascular events in life-style related diseases by suppressing the activation of monocytes/macrophages and/or MCP-1 production via CD40. In particular, in a long- term continuous administration, they can suppress the onset of cardiovascular events by an action different from that of the conventional low cholesterol therapy based on HMG-CoA reductase inhibitors. According to the method of the present invention, it is possible to screen agents that reduce risks of cardiovascular events.

What is claimed is:

1. A method for prevention or treatment of life-style related diseases by administering to a mammal an effective amount of a CD40 signal blocking agent that is an s-triazolo(1,5-a)pyrimidine derivative represented by formula (1):

(1)

or at least one pharmaceutically acceptable salt thereof, wherein $R_1$ is H, halo, $C_1$–$C_4$ alkyl, alkoxyalkyl, aralkyl, aryl, substituted aryl, or $NR_5R_6$;

$R_2$ is H, halo, $C_1$–$C_4$ alkyl, alkenyl, aralkyl, or aryl;

$R_3$ is amino or substituted amino with one substituent or two substituents that are the same or different, which substituents are selected from alkyl, cycloalkyl, alkenyl, hydroxyalkyl, alkylaminoalkyl or alkoxy, an optionally substituted aryl group, an aralkyl group, a heterocyclic group, or $R_3$ is hydrazino, guanidino, tertiary cyclic amino, a linear or branched alkoxy group having 2–4 carbons substituted with a basic group in which said basic group is the above amino group, a substituted amino group, a guanidino group, a hydrazino group or a cyclic amino group, or $NR_7R_8$;

$R_4$ is H, halo, $C_1$–$C_4$ alkyl, alkoxyalkyl, aralkyl, aryl, or substituted aryl;

$R_5$ and $R_6$ are H, $C_1$–$C_5$ linear or branched alkyl groups, or $R_5$ and $R_6$, together with a heteroatom, form a ring;

$R_7$ is $C_4$–$C_9$ linear or branched alkyl, $C_1$–$C_3$ alkoxy or alkyl substituted aralkyl, 2,5-dioxaheptyl, or 3-oxahexyl;

$R_8$ is H, $C_1$–$C_3$ alkyl, hydroxyethyl, or hydroxypropyl;

provided that when $R_1$ is $NR_5R_6$ and $R_3$ is $NR_7R_8$, substituents at positions 5 and 7 are interchangeable;

said blocking agent having at least one of the following effects:

a) an effect of blocking the CD40 pathway for monocyte/macrophage activation,
b) an effect of suppressing CD40 expression,
c) an effect of suppressing IL-6 production,
d) an effect of suppressing Il-12 production, or
e) an effect of suppressing MCP-1 production.

2. A method for screening agents that reduce risk of cardiovascular events in life-style related diseases, comprising:

a) comparing at least one of the following parameters of a test compound to trapidil for the ability to:
   down-regulate CD40
   suppress CD40 mRNA expression,
   suppress IL-6 production by monocytes
   suppress IL-12 production by monocytes
   suppress MCP-1 production or
b) selecting test compounds that are equal to or better than trapidil in at least one of the parameters.

3. A method according to claim 1, wherein the life-style related disease is insulin non-dependent diabetes mellitus.

4. A method according to claim 1, wherein the life-style related disease is obesity.

5. A method according to claim 1, wherein the life-style related disease is hyperlipemia.

6. A method according to claim 1, wherein the life-style related disease is an alcoholic liver disease.

7. A method for prevention or treatment of cardiovascular events in life-style related diseases, the method comprising administering to a mammal an effective amount of a CD40 signal blocking agent that is an s-triazolo(1,5-a)pyrimidine derivative of formula (1):

(1)

or at least one pharmaceutically acceptable salt thereof, wherein $R_1$ is H, halo, $C_1$–$C_4$ alkyl, alkoxyalkyl, aralkyl, aryl, substituted aryl, or $NR_5R_6$;

$R_2$ is H, halo, $C_1$–$C_4$ alkyl, alkenyl, aralkyl, or aryl;

$R_3$ is amino or substituted amino with one substituent or two substituents that are the same or different, which substituents are selected from alkyl, cycloalkyl, alkenyl, hydroxyalkyl, alkylaminoalkyl or alkoxy, an optionally substituted aryl group, an aralkyl group, a heterocyclic group, or $R_3$ is hydrazino, guanidino, tertiary cyclic amino, a linear or branched alkoxy group having 2–4 carbons substituted with a basic group in which said basic group is the above amino group, a substituted amino group, a guanidino group, a hydrazino group, a cyclic amino group, or $NR_7R_8$;

$R_4$ is H, halo, $C_1$–$C_4$ alkyl, alkoxyalkyl, aralkyl, aryl, or substituted aryl;

$R_5$ and $R_6$ are H, $C_1$–$C_5$ linear or branched alkyl groups, or $R_5$ and $R_6$, together with a heteroatom, form a ring;

$R_7$ is $C_4$–$C_9$ linear or branched alkyl, $C_1$–$C_3$ alkoxy or alkyl substituted aralkyl, 2,5-dioxaheptyl, or 3-oxahexyl;

$R_8$ is H, $C_1$–$C_3$ alkyl, hydroxyethyl, or hydroxypropyl;

provided that when $R_1$ is $NR_5R_6$ and $R_3$ is $NR_7R_8$, substituents at positions 5 and 7 are interchangeable;

said blocking agent having at least one of the following effects:

a) an effect of blocking the CD40 pathway for monocyte/macrophage activation,
b) an effect of suppressing CD40 expression,
c) an effect of suppressing IL-6 production,
d) an effect of suppressing Il-12 production, or
e) an effect of suppressing MCP-1 production.

8. A method according to claim 7 wherein the cardiovascular event is based on coronary artery diseases.

9. method for prevention or treatment of cerebrovascular diseases by administering to a mammal an effective amount of a CD40 signal blocking agent that is an s-triazolo(1,5-a) pyrimidine derivative represented by formula (1):

(1)

or at least one pharmaceutically acceptable salt thereof, wherein $R_1$ is H, halo, $C_1$–$C_4$ alkyl, alkoxyalkyl, aralkyl, aryl, substituted aryl, or $NR_5R_6$;

$R_2$ is H, halo, $C_1$–$C_4$ alkyl, alkenyl, aralkyl, or aryl;

$R_3$ is amino or substituted amino with one substituent or two substituents that are the same or different, which substituents are selected from alkyl, cycloalkyl, alkenyl, hydroxyalkyl, alkylaminoalkyl or alkoxy, an optionally substituted aryl group, an aralkyl group, a heterocyclic group, or $R_3$ is hydrazino, guanidino, tertiary cyclic amino, a linear or branched alkoxy group having 2–4 carbons substituted with a basic group in which said basic group is the above amino group, a substituted amino group, a guanidino group, a hydrazino group, a cyclic amino group, or $NR_7R_8$;

$R_4$ is H, halo, $C_1$–$C_4$ alkyl, alkoxyalkyl, aralkyl, aryl, or substituted aryl;

$R_5$ and $R_6$ are H, $C_1$–$C_5$ linear or branched alkyl groups, or $R_5$ and $R_6$, together with a heteroatom, form a ring;

$R_7$ is $C_4$–$C_9$ linear or branched alkyl, $C_1$–$C_3$ alkoxy or alkyl substituted aralkyl, 2,5-dioxaheptyl, or 3-oxahexyl;

$R_8$ is H, $C_1$–$C_3$ alkyl, hydroxyethyl, or hydroxypropyl;

provided that when $R_1$ is $NR_5R_6$ and $R_3$ is $NR_7R_8$, substituents at positions 5 and 7 are interchangeable;

said blocking agent having at least one of the following effects:
a) an effect of blocking the CD40 pathway for monocyte/macrophage activation,
b) an effect of suppressing CD40 expression,
c) an effect of suppressing IL-6 production,
d) an effect of suppressing Il-12 production, or
e) an effect of suppressing MCP-1 production.

10. A method of blocking the CD40 pathway for monocyte/macrophage activation by applying an effective amount of a CD40 signal blocking agent that is an s-triazolo (1,5-a)pyrimidine derivative represented by formula (1):

(1)

or at least one pharmaceutically acceptable salt thereof, wherein $R_1$ is H, halo, $C_1$–$C_4$ alkyl, alkoxyalkyl, aralkyl, aryl, substituted aryl, or $NR_5R_6$;

$R_2$ is H, halo, $C_1$–$C_4$ alkyl, alkenyl, aralkyl, or aryl;

$R_3$ is amino or substituted amino with one substituent or two substituents that are the same or different, which substituents are selected from alkyl, cycloalkyl, alkenyl, hydroxyalkyl, alkylaminoalkyl or alkoxy, an optionally substituted aryl group, an aralkyl group, a heterocyclic group, or $R_3$ is hydrazino, guanidino, tertiary cyclic amino, a linear or branched alkoxy group having 2–4 carbons substituted with a basic group in which said basic group is the above amino group, a substituted amino group, a guanidino group, a hydrazino group, a cyclic amino group, or $NR_7R_8$;

$R_4$ is H, halo, $C_1$–$C_4$ alkyl, alkoxyalkyl, aralkyl, aryl, or substituted aryl;

$R_5$ and $R_6$ are H, $C_1$–$C_5$ linear or branched alkyl groups, or $R_5$ and $R_6$, together with a heteroatom, form a ring;

$R_7$ is $C_4$–$C_9$ linear or branched alkyl, $C_1$–$C_3$ alkoxy or alkyl substituted aralkyl, 2,5-dioxaheptyl, or 3-oxahexyl;

$R_8$ is H, $C_1$–$C_3$ alkyl, hydroxyethyl, or hydroxypropyl;

provided that when $R_1$ is $NR_5R_6$ and $R_3$ is $NR_7R_8$, substituents at positions 5 and 7 are interchangeable;

said blocking agent having at least one of the following effects:
a) an effect of blocking the CD40 pathway for monocyte/macrophage activation,
b) an effect of suppressing CD40 expression,
c) an effect of suppressing IL-6 production,
d) an effect of suppressing Il-12 production, or
e) an effect of suppressing MCP-1 production.

11. A method of suppressing CD40 expression by applying an effective amount of a CD40 signal blocking agent that is an s-triazolo(1,5-a)pyrimidine derivative represented by formula (1):

(1)

or at least one pharmaceutically acceptable salt thereof, wherein $R_1$ is H, halo, $C_1$–$C_4$ alkyl, alkoxyalkyl, aralkyl, aryl, substituted aryl, or $NR_5R_6$;

$R_2$ is H, halo, $C_1$–$C_4$ alkyl, alkenyl, aralkyl, or aryl;

$R_3$ is amino or substituted amino with one substituent or two substituents that are the same or different, which substituents are selected from alkyl, cycloalkyl, alkenyl, hydroxyalkyl, alkylaminoalkyl or alkoxy, an optionally substituted aryl group, an aralkyl group, a heterocyclic group, or $R_3$ is hydrazino, guanidino, tertiary cyclic amino, a linear or branched alkoxy group having 2–4 carbons substituted with a basic group in which said basic group is the above amino group, a substituted amino group, a guanidino group, a hydrazino group, a cyclic amino group, or $NR_7R_8$;

$R_4$ is H, halo, $C_1$–$C_4$ alkyl, alkoxyalkyl, aralkyl, aryl, or substituted aryl;

$R_5$ and $R_6$ are H, $C_1$–$C_5$ linear or branched alkyl groups, or $R_5$ and $R_6$, together with a heteroatom, form a ring;

$R_7$ is $C_4$–$C_9$ linear or branched alkyl, $C_1$–$C_3$ alkoxy or alkyl substituted aralkyl, 2,5-dioxaheptyl, or 3-oxahexyl;

$R_8$ is H, $C_1$–$C_3$ alkyl, hydroxyethyl, or hydroxypropyl;

provided that when $R_1$ is $NR_5R_6$ and $R_3$ is $NR_7R_8$, substituents at positions 5 and 7 are interchangeable;

said blocking agent having at least one of the following effects:
 a) an effect of blocking the CD40 pathway for monocyte/macrophage activation,
 b) an effect of suppressing CD40 expression,
 c) an effect of suppressing IL-6 production,
 d) an effect of suppressing Il-12 production, or
 e) an effect of suppressing MCP-1 production.

12. A method of suppressing IL-6 production by applying an effective amount of a CD40 signal blocking agent that is an s-triazolo(1,5-a)pyrimidine derivative represented by formula (1):

(1)

or at least one pharmaceutically acceptable salt thereof, wherein $R_1$ is H, halo, $C_1$–$C_4$ alkyl, alkoxyalkyl, aralkyl, aryl, substituted aryl, or $NR_5R_6$;

$R_2$ is H, halo, $C_1$–$C_4$ alkyl, alkenyl, aralkyl, or aryl;

$R_3$ is amino or substituted amino with one substituent or two substituents that are the same or different, which substituents are selected from alkyl, cycloalkyl, alkenyl, hydroxyalkyl, alkylaminoalkyl or alkoxy, an optionally substituted aryl group, an aralkyl group, a heterocyclic group, or $R_3$ is hydrazino, guanidino, tertiary cyclic amino, a linear or branched alkoxy group having 2–4 carbons substituted with a basic group in which said basic group is the above amino group, a substituted amino group, a guanidino group, a hydrazino group, a cyclic amino group, or $NR_7R_8$;

$R_4$ is H, halo, $C_1$–$C_4$ alkyl, alkoxyalkyl, aralkyl, aryl, or substituted aryl;

$R_5$ and $R_6$ are H, $C_1$–$C_5$ linear or branched alkyl groups, or $R_5$ and $R_6$, together with a heteroatom, form a ring;

$R_7$ is $C_4$–$C_9$ linear or branched alkyl, $C_1$–$C_3$ alkoxy or alkyl substituted aralkyl, 2,5-dioxaheptyl, or 3-oxahexyl;

$R_8$ is H, $C_1$–$C_3$ alkyl, hydroxyethyl, or hydroxypropyl;

provided that when $R_1$ is $NR_5R_6$ and $R_3$ is $NR_7R_8$, substituents at positions 5 and 7 are interchangeable;

said blocking agent having at least one of the following effects:
 a) an effect of blocking the CD40 pathway for monocyte/macrophage activation,
 b) an effect of suppressing CD40 expression,
 c) an effect of suppressing IL-6 production,
 d) an effect of suppressing Il-12 production, or
 e) an effect of suppressing MCP-1 production.

13. A method of suppressing IL-12 production by applying an effective amount of a CD40 signal blocking agent that is an s-triazolo(1,5-a)pyrimidine derivative represented by formula (1):

(1)

or at least one pharmaceutically acceptable salt thereof, wherein $R_1$ is H, halo, $C_1$–$C_4$ alkyl, alkoxyalkyl, aralkyl, aryl, substituted aryl, or $NR_5R_6$;

$R_2$ is H, halo, $C_1$–$C_4$ alkyl, alkenyl, aralkyl, or aryl;

$R_3$ is amino or substituted amino with one substituent or two substituents that are the same or different, which substituents are selected from alkyl, cycloalkyl, alkenyl, hydroxyalkyl, alkylaminoalkyl or alkoxy, an optionally substituted aryl group, an aralkyl group, a heterocyclic group, or $R_3$ is hydrazino, guanidino, tertiary cyclic amino, a linear or branched alkoxy group having 2–4 carbons substituted with a basic group in which said basic group is the above amino group, a substituted amino group, a guanidino group, a hydrazino group, a cyclic amino group, or $NR_7R_8$;

$R_4$ is H, halo, $C_1$–$C_4$ alkyl, alkoxyalkyl, aralkyl, aryl, or substituted aryl;

$R_5$ and $R_6$ are H, $C_1$–$C_5$ linear or branched alkyl groups, or $R_5$ and $R_6$, together with a heteroatom, form a ring;

$R_7$ is $C_4$–$C_5$ linear or branched alkyl, $C_1$–$C_3$ alkoxy or alkyl substituted aralkyl, 2,5-dioxaheptyl, or 3-oxahexyl;

$R_8$ is H, $C_1$–$C_3$ alkyl, hydroxyethyl, or hydroxypropyl;

provided that when $R_1$ is $NR_5R_6$ and $R_3$ is $NR_7R_8$, substituents at positions 5 and 7 are interchangeable;

said blocking agent having at least one of the following effects:
 a) an effect of blocking the CD40 pathway for monocyte/macrophage activation,
 b) an effect of suppressing CD40 expression,
 c) an effect of suppressing IL-6 production,
 d) an effect of suppressing Il-12 production, or
 e) an effect of suppressing MCP-1 production.

14. A method of suppressing MCP-1 production by applying an effective amount of a CD40 signal blocking agent that is an s-triazolo(1,5-a)pyrimidine derivative represented by formula (1):

(1)

or at least one pharmaceutically acceptable salt thereof, wherein $R_1$ is H, halo, $C_1$–$C_4$ alkyl, alkoxyalkyl, aralkyl, aryl, substituted aryl, or $NR_5R_6$;

$R_2$ is H, halo, $C_1$–$C_4$ alkyl, alkenyl, aralkyl, or aryl;

$R_3$ is amino or substituted amino with one substituent or two substituents that are the same or different, substituents are selected from alkyl, cycloalkyl, alkenyl, hydroxyalkyl, alkylaminoalkyl or alkoxy, an optionally substituted aryl group, an aralkyl group, a heterocyclic group, or $R_3$ is hydrazino, guanidino, tertiary cyclic amino, a linear or branched alkoxy group having 2–4 carbons substituted with a basic group in which said basic group is the above amino group, a substituted amino group, a guanidino group, a hydrazino group, a cyclic amino group, or $NR_7R_8$;

$R_4$ is H, halo, $C_1$–$C_4$ alkyl, alkoxyalkyl, aralkyl, aryl, or substituted aryl;

$R_5$ and $R_6$ are H, $C_1$–$C_5$ linear or branched alkyl groups, or $R_5$ and $R_6$, together with a heteroatom, form a ring;

$R_7$ is $C_4$–$C_9$ linear or branched alkyl, $C_1$–$C_3$ alkoxy or alkyl substituted aralkyl, 2,5-dioxaheptyl, or 3-oxahexyl;

$R_8$ is H, $C_1$–$C_3$ alkyl, hydroxyethyl, or hydroxypropyl;

provided that when $R_1$ is $NR_5R_6$ and $R_3$ is $NR_7R_8$, substituents at positions 5 and 7 are interchangeable;

said blocking agent having at least one of the following effects:
a) an effect of blocking the CD40 pathway for monocyte/macrophage activation,
b) an effect of suppressing CD40 expression,
c) an effect of suppressing IL-6 production,
d) an effect of suppressing II-12 production, or
e) an effect of suppressing MCP-1 production.

15. A method of suppressing atherogenic plaque formation at a damaged site of a blood vessel by applying an effective amount of a CD40 signal blocking agent that is an s-triazolo(1,5-a)pyrimidine derivative represented by formula (1):

(1)

or at least one pharmaceutically acceptable salt thereof, wherein $R_1$ is H, halo, $C_1$–$C_4$ alkyl, alkoxyalkyl, aralkyl, aryl, substituted aryl, or $NR_5R_6$;

$R_2$ is H, halo, $C_1$–$C_4$ alkyl, alkenyl, aralkyl, or aryl;

$R_3$ is amino or substituted amino with one substituent or two substituents that are the same or different, which substituents are selected from alkyl, cycloalkyl, alkenyl, hydroxyalkyl, alkylaminoalkyl or alkoxy, an optionally substituted aryl group, an aralkyl group, a heterocyclic group, or $R_3$ is hydrazino, guanidino, tertiary cyclic amino, a linear or branched alkoxy group having 2–4 carbons substituted with a basic group in which said basic group is the above amino group, a substituted amino group, a guanidino group, a hydrazino group, a cyclic amino group, or $NR_7R_8$;

$R_4$ is H, halo, $C_1$–$C_4$ alkyl, alkoxyalkyl, aralkyl, aryl, or substituted aryl;

$R_5$ and $R_6$ are H, $C_1$–$C_5$ linear or branched alkyl groups, or $R_5$ and $R_6$, together with a heteroatom, form a ring;

$R_7$ is $C_4$–$C_9$ linear or branched alkyl, $C_1$–$C_3$ alkoxy or alkyl substituted aralkyl, 2,5-dioxaheptyl, or 3-oxahexyl;

$R_8$ is H, $C_1$–$C_3$ alkyl, hydroxyethyl, or hydroxypropyl;

provided that when $R_1$ is $NR_5R_6$ and $R_3$ is $NR_7R_8$, substituents at positions 5 and 7 are interchangeable;

said blocking agent having at least one of the following effects:
a) an effect of blocking the CD40 pathway for monocyte/macrophage activation,
b) an effect of suppressing CD40 expression,
c) an effect of suppressing IL-6 production,
d) an effect of suppressing II-12 production, or
e) an effect of suppressing MCP-1 production.

16. A method for prevention or treatment of life-style related diseases by administering to a mammal an effective amount of a CD40 signal blocking agent that is an s-triazolo (1,5-a)pyrimidine derivative represented by formula (1):

(1)

or at least one pharmaceutically acceptable salt thereof, wherein $R_1$ is H, methyl, ethyl, phenyl, piperidino, dimethylamino, or morpholino;

$R_2$ is H, chloro, or bromo;

$R_3$ is diethylamino, isobutylamino, benzylamino, furfurylamino, n-amylamino, diethanolamino, piperidino, o-chloroanilino, p-carboethoxyanilino, β-diethylamino-ethoxy, N-(n-butyl)-N-(β-hydroxyethyl)-amino, N-(n-pentyl)-N-(β-hydroxyethyl)-amino, N-(n-hexyl)-N-(β-hydroxyethyl)-amino, or a N-(ethoxyethyl)-N-(β-hydroxyethyl)-amino;

$R_4$ is H, methyl, ethyl, isopropyl, phenyl, or 3,4,5-trimethoxyphenyl.

17. A method for prevention or treatment of life-style related diseases by administering to a mammal an effective amount of a CD40 signal blocking agent or at least one pharmaceutically acceptable salt thereof, selected from the group consisting of:

7-diethylamino-s-triazolo(1,5-a)pyrimidine;
7-benzylamino-s-triazolo(1,5-a)pyrimidine;
2-ethyl-5-methyl-7-diethylamino-s-triazolo(1,5-a) pyrimidine;
5-methyl-6-chloro-7-furfurylamino-s-triazolo(1,5-a) pyrimidine;
5-methyl-6-bromo-7-diethylamino-s-triazolo(1,5-a) pyrimidine;
5-methyl-7-(β-diethylamino-ethoxy-s-triazolo(1,5-a) pyrimidine;
2-isopropyl-5-methyl-7-piperidino-s-triazolo(1,5-a) pyrimidine;
5-methyl-7-n-amyl-amino-s-triazolo(1,5-a)pyrimidine;
2-(3',4',5'-trimethoxy-phenyl)-5-methyl-7-piperidino-s-triazolo(1,5-a)pyrimidine;
5-phenyl-7-diethanolamino-s-triazolo(1,5-a)pyrimidine;
2-phenyl-5-methyl-7-piperidino-s-triazolo(1,5-a) pyrimidine;
5-methyl-7-(o-chloro-anilino)-s-triazolo(1,5-a)pyrimidine;
7-(p-carboethoxy-anilino)-5-methyl-s-triazolo(1,5-a) pyrimidine;
N,N-diethyl-N'-[5-methyl-6-bromo-s-triazolo(1,5-a) pyrimidinyl-(7)]-propylene diamine;

5-methyl-7-benzylamino-s-triazolo(1,5-a)pyrimidine;
2,5-dimethyl-7-furfuryl-amino-s-triazolo(1,5-a)pyrimidine;
2,5-dimethyl-7-benzylamino-s-triazolo(1,5-a)pyrimidine;
2,5-dimethyl-7-piperidino-s-triazolo(1,5-a)pyrimidine;
5-methyl-7-diethylamino-s-triazolo(1,5-a)pyrimidine;
2,5-dimethyl-7-isobutyl-amino-s-triazolo(1,5-a)pyrimidine;
5-piperidino-7-(N-(n-pentyl)-N-($\beta$-hydroxyethyl)-amino-s-triazolo(1,5-a)pyrimidine;
5-diethylamino-7-(N-(n-pentyl)-N-($\beta$-hydroxyethyl)-amino)-s-triazolo(1,5-a)pyrimidine;
5-diethylamino-7-(N-(n-hexyl)-N-($\beta$-hydroxyethyl)amino-s-triazolo(1,5-a)pyrimidine;
5-piperidino-7-(N-(n-hexyl)-N-($\beta$-hydroxyethyl)amino)-s-triazolo(1,5-a)pyrimidine;
5-morpholino-7-(N-(n-butyl)-N-($\beta$-hydroxyethyl)-amino)-s-triazolo(1,5-a)pyrimidine;
5-piperidino-74-(N-ethoxyethyl)-N-($\beta$-hydroxyethyl)amino)-s-triazolo(1,5a)pyrimidine; and
5-diethylamino-7-(ethoxyethyl)-N-($\beta$-hydroxyethyl)-amino-s-triazolo(1,5a)pyrimidine.

18. A method of claim 1 wherein the CD40 blocking agent is administered in combination with one or more drugs used for suppressing cardiovascular events.

19. A method of claim 1 wherein the CD40 blocking agent is administered orally in a tablet, sugar coated tablet, sustained release tablet, film coated tablet, parvule, granule, powder, capsule, syrup, elixir, or poti formulation.

20. A method of claim 1 wherein the CD40 blocking agent is administered parenterally by intravenous, intra-arterial, intradermal, or subcutaneous injection.

21. A method of claim 1 wherein the CD40 blocking agent is administered by intradermal implant.

22. A method of claim 1 wherein the CD40 blocking agent is administered transmucously in a sublingual tablet, chewing gum, or suppository.

23. A method of claim 1 whereby the unit dosage for a non-sustained release formulation is 10 mg, 50 mg, 100 mg, 200 mg, 300 mg, 400 mg, or 500 mg; and the unit dosage for a sustained release formulation is 700 mg, 800 mg, 900 mg, 1000 mg, 1100 mg, or 1200 mg.

\* \* \* \* \*